US005891860A

United States Patent [19]
Heerze et al.

[11] Patent Number: 5,891,860
[45] Date of Patent: Apr. 6, 1999

[54] TREATMENT OF TRAVELLER'S DIARRHEA

[75] Inventors: Louis D. Heerze; Glen D. Armstrong, both of Alberta, Canada

[73] Assignee: Synsorb Biotech, Inc., Calgary, Canada

[ * ] Notice: The term of this patent shall not extend beyond the expiration date of Pat. Nos. 5,637,576 and 5,627,163.

[21] Appl. No.: 973,443

[22] PCT Filed: Mar. 11, 1996

[86] PCT No.: PCT/CA96/00144

§ 371 Date: Apr. 16, 1998

§ 102(e) Date: Apr. 16, 1998

[87] PCT Pub. No.: WO96/39189

PCT Pub. Date: Dec. 12, 1996

[51] Int. Cl.$^6$ ................................................. A61K 31/715
[52] U.S. Cl. .............................. 514/53; 514/54; 514/61; 514/867; 536/123; 536/123.1; 536/123.13
[58] Field of Search ................................. 514/53, 54, 61; 514/867; 536/123, 123.1, 123.13

[56] References Cited

U.S. PATENT DOCUMENTS

| | | | |
|---|---|---|---|
| 4,137,401 | 1/1979 | Lemieux et al. | 536/116 |
| 4,238,473 | 12/1980 | Lemieux et al. | 424/11 |
| 4,362,720 | 12/1982 | Lemieux et al. | 424/180 |
| 5,079,353 | 1/1992 | Ratcliffe et al. | 536/123 |
| 5,627,163 | 5/1997 | Heerze et al. | 514/61 |
| 5,637,576 | 6/1997 | Heerze et al. | 514/61 |

FOREIGN PATENT DOCUMENTS

| | | |
|---|---|---|
| WO93/08209 | 4/1993 | WIPO . |
| WO95/21628 | 8/1995 | WIPO . |

OTHER PUBLICATIONS

Abbas, S.A., et al., "Tumor–Associated Oligosaccharides I: Synthesis of Sialyl–Lewis$^a$ Antigenic Determinant", *Sialic Acids, Proc. Japan–German Symp. Berlin*, pp. 22–23 (1988).

Amvam–Zollo, P., et al., "Streptococcus pneumoniae Type XIV Polysaccharide: Synthesis of a Repeating Branched Tetrasaccharide with Dioxa–Type Spacer–Arms", *Carbohy. Res.*, 150:199–212 (1986).

Armstrong, G.D., et al., "Investigation of shiga–like toxin binding to chemically synthesized oligosaccharide sequences", *J. Infect. Dis.*, 164:1160–1167 (1991).

Bartus, H., et al., "Indications that the erythrocyte receptor involved in enterotoxigenic *Escherichia coli* attachment is a sialoglycoconjugate", *J. Clin. Microb.*, 21(6):951–954 (1985).

Bourgeois, A.L., et al., "Etiology of acute diarrhea among United States military personnel deployed to South America and West Africa", *Am. J. Trop. Med. Hyg.*, 48(2):243–248 (1993).

Chernyak, A.Y., et al., "A New Type of Carbohydrate–Containing Synthetic Antigen: Synthesis of Carbohydrate–Containing Polyacrylamide Copolymers having the Specificity of 0:3 and 0:4 Factors of Salmonella", *Carbohy. Res.*, 128:269–282 (1984).

Cox, D., et al. "A New Synthesis of 4–O–α–D–Galactopyransoyl–D–Galacto–Pyranose", *Carbohy. Res.*, 62:245–252 (1978).

Dahmén, J., et al., "2–Bromoethyl glycosides: applications in the synthesis of spacer–arm glycosides", *Carbohy. Res.*, 118:292–301 (1983).

Dahmén, J., et al., "Synthesis of space arm, lipid, and ethyl glycosides of the trisaccharide portion [α–D–Gal–(1–4)–β–D–Gal(1–4)–β–D–Glc] of the blood group p$^k$ antigen: preparation of neoglycoproteins", *Carbohy. Res.*, 127:15–25 (1984).

Database Biosis, Biosciences Information Service, Pediatric Nephrology, 9(6):p.C30 (1995).

Ekborg, G., et al., "Synthesis of Three Disaccharides for the Preparation of Immunogens bearing Immunodeterminants Known to Occur on Glycoproteins", *Carbohy. Res.*, 110:55–67.

Ericsson, C.D., et al., "Travelers' Diarrhea: Approaches to prevention and treatment", *Clin. Infect. Dis.*, 16:616–626 (1993).

Fernandez–Santana, V., et al., "Glycosides of Monoallyl Diethylene Glycol. A New type of Spacer group for Synthetic Oligosaccharides", *J. Carboh. Chem.*, 8(3):531–537 (1989).

Fishman, P.H., et al., "Gangliosides as Receptors for Bacterial Entertoxins", *Advances in Lipid Res.*, 25:165–187 (1993).

Fügedi, P., et al., "Thioglycosides as Glycosylating Agents in Oligosaccharide Synthesis", *Glycocon. J.*, 4:97–108(1987).

Fukuta, S., et al., "Comparison of the carbohydrate–binding specificities of cholera toxin and *Escherichia coli* heat––labile enterotoxins LTh–I,LTh–IIa, and LTh–IIb", *Infect. Immun.*, 56(7):1748–1753 (1988).

Garegg, P.J., et al., "A Synthesis of 8–Methoxycarbonyloct–1–yl O–α–D–Galactopyranosyl–(1–3)

(List continued on next page.)

Primary Examiner—Howard C. Lee
Attorney, Agent, or Firm—Burns, Doane, Swecker & Mathis, L.L.P.

[57] ABSTRACT

This invention relates to treatment of traveller's diarrhea, including diarrhea caused by enterotoxigenic *Escherichia coli* (ETEC), using an oligosaccharide-containing composition. The composition contains an oligosaccharide sequence covalently attached to a pharmaceutically acceptable solid, inert support through a non-peptidyl compatible linker arm. The oligosaccharide-containing composition binds *E. coli* heat-labile toxin (LT). More specifically, the invention concerns neutralization and removal of LT associated with traveller's diarrhea.

15 Claims, 5 Drawing Sheets

OTHER PUBLICATIONS

–O–β–D–Galactopyranosyl–(1–4)–2–Acetamido–2–Deoxy–β–D–Glucopyranoside", *Carbohy. Res.*, 136:207–213 (1985).

Garegg, P.J., et al., "Synthesis of 6– and 6' –deoxy derivatives of methyl 4–O–α–D–galactopyranosyl–β–D–galactopyranoside for studies of inhibition of pyelonephritogenic fimbriated *E. coli* adhesion to urinary epitheluim–cell surfaces", *Carbohy. Res.*, 137:270–275 (1985).

Heerze, L.D., et al., "Oligosaccharide sequences attached to an inert support (SYNSORB) as potential therapy for antibiotic–associated diarrhea and pseudomembranous colitis", *J. Infect. Dis.*, 169:1291–1296 (1994).

Huilan, S., et al., "Etiology of acute diarrhoea among children in developing countries — a multicenter study in five countries", *Bulletin of the World Health Organisation*, 69:549–555 (1991).

Jacquinet, J.C., et al., "Synthesis of Blood–group Substances, Part 11. Synthesis of the Trisaccharide O–α–D–Galactopyranosyl–(1–3)–O–β–D–galactopyranosyl–(1–4)–2–acetamido–2–deoxy–D–glucopyranose", *J.C.S. Perkin*, 1:326–330 (1981).

Kameyama, A., et al., "Total synthesis of sialyl Lewis X", *Carbohy. Res.*, 209:c1–c4 (1991).

Koike, K., et al., "Total Synthesis of Globotriaosyl–E and Z–Ceramides and Isoglobotriaosyl–E–Ceramide", *Carbohy. Res.*, 163:189–208 (1987).

Lee, R.T., et al., "Synthesis of 3–(2–Aminoethylthio) PropylGlycosides", *Carbohy. Res.*, 37:193–201 (1974).

Lemieux, R.U., et al., "The properties of a 'synthetic' antigen related to the blood–group Lewis A", *J. Am. Chem. Soc.*, 97(14):4076–4083 (1975).

Merrit, E.A., et al., "Galactose–binding site in *Escherichia coli* heat–labile enterotoxin (LT) and cholera toxin (CT)", *Mol. Microb.*, 13(4):745–753 (1994).

Okamoto, K., et al., "Glycosidation of Sialic Acid", *Tetrahedron*, 46(17):5835–5857 (1990).

Orlandi, P.A., et al., "The Heat–Labile Enterotoxin of *Escherichia coli* Binds to Polylactosaminoglycan–Containing Receptors in CaCo–2 Human Intestinal Epithelial Cells", *Biochem.*, 33:12886–12895 (1994).

Oro, H.S., et al., "Identification of asialo GM1 as a binding structure for *Escherichia coli* colonization factor antigens", *FEMS Microb. Lett.*, 72:289–292 (1990).

Paulsen, H., "Advances in Selective Chemical Syntheses of Complex Oligosaccharides", *Angew. Chem. Int. Ed. Eng.*, 21(3):155–173 (1982).

Paulsen, H., "Synthese von oligosaccharid–determinanten mit amid–spacer vom typ des T–antigens", *Carbohy. Res.*, 104:195–219 (1982).

Peltola, H., et al., "Prevention of traveller's diarrhoea by oral B subunit/whole–cell cholera vaccine", *Lancet*, 338:1285–1289 (1991).

Rana, S.S., et al., "Synthesis of Phenyl 2–Acetamido–2–Deoxy–3–O–α–L–Fucopyranosyl–β–D–Glucopyranoside and Related Compounds", *Carbohy Res.*, 91:149–157 (1981).

Schaubach, R., et al., "Tumor–Associated Antigen Synthesis: Synthesis of the Gal–α–(1–3)–Gal–β–(1–4)–GlcNAc Epitope. A specific Determinant for Metastatic Progression?", *Liebigs Ann. Chem.*, p. 607–614 (1991).

Schengrund, C–L., et al., "Binding of Vibrio cholera toxin and heat–labile enterotoxin of *Escherichia coli* to GM1, derivatives of GM1 and nonlipid oligosaccharide polyvalent ligands", *J. Biol. Chem.*, 264(22):13233–13237 (1989).

Schmidt, R.R., "New Methods for the Synthesis of Glycosides and Oligosaccharides — Are There Alternatives to the Koenigs–Knorr Method?", *Agnew. Chem. Int. Ed. Eng.*, 25:212–235 (1986).

Shida, K., et al., "*Escherichia coli* heat–labile enterotoxin binds to glycosylated proteins with lactose by aminocarbonyl reaction", *Microbl. Immun.*, 38(4):273–279 (1994).

Sixma, T.K., et al., "Lactose binding to heat–labile enterotoxin from *E. coli*", *Nature*, 355:561–564(1992).

Spangler, B.D., "Structure and Function of Cholera Toxin and the Related *Escherichia coli* Heat–Labile Enterotoxin", *Microb. Rev.*, 56(4):622–647 (1992).

Uesaka, Y., et al., "Simple method of purification of *Escherichia coli* heat–labile enterotoxin and cholera toxin using immobilized galactose", *Microb. Path.*, 16:71–76 (1994).

Wenneras, C., et al., "Binding of fibrillar CS3 adhesin of enterotoxigenic *Escherichia coli* to rabbit intestinal glycoproteins is competitively prevented by GalNAc(1–4)Gal containing glycoconjugates", *Infect. Immun.*, 63(2):640–646 (1995).

Wolf, M.K., et al., "Characterization of enterotoxigenic *Escherichia coli* isolated from U.S. troops deployed to the middle east", *J. Clin. Microb.*, 31(4):851–856 (1993).

TREATMENT OF TRAVELLER'S DIARRHEA

FIELD OF THE INVENTION

This invention relates to treatment of traveller's diarrhea, including diarrhea caused by enterotoxigenic *Escherichia coli* (ETEC). More specifically, the invention concerns neutralization and removal of *E. coli* heat-labile toxin (LT) associated with ETEC. This invention also relates to prevention of ETEC, the causative agent of traveller's diarrhea from colonizing the intestinal tract.

REFERENCES

The following references are cited in the application as numbers in brackets ([ ]) at the relevant portion of the application.

1. Peltola, H., et al., Prevention of traveller's diarrhoea by oral B subunit/whole-cell cholera vaccine Lancet: 338, 1285–1289 (1991).

2. Ericsson, C. D. et al., Travelers' Diarrhea: Approaches to prevention and treatment. Clin. Infec. Dis: 16, 616–626 (1993).

3. Spangler, Brenda D., "Structure and Function of Cholera Toxin and the related *Escherichia coli* Heat-Labile Enterotoxin" Microbiological Reviews, 56, No. 4:622–647 (1992).

4. Huilan, S., et al., Etiology of acute diarrhoea among children in developing countries—a multicenter study in five countries., J. Clin. Microbiol. 31: 851–856 (1993).

5. Wolf, M. K. et al., Characterization of enterotoxigenic *Escherichia coli* isolated from U.S. troops deployed to the middle east., J. Clin. Microbiol. 31: 851–856 (1993).

6. Bourgeois, A. L. et al., Etiology of acute diarrhea among United States military personnel deployed to South America and West Africa, Am. J. Trop. Med. Hyg. 48: 243–248 (1993).

7. Orlandi, Palmer A., et al., "The Heat-Labile Enterotoxin of *Escherichia coli* Binds to Polylactosaminoglycan-Containing Receptors in CaCo-2 Human Intestinal Epithelial Cells", Biochemistry, 33:12886–12895 (1994).

8. Fishman, Peter H., "Gangliosides as Receptors for Bacterial Enterotoxins", Advances in Lipid Research, 25:165–187 (1993).

9. Bartus, H., et al., Indications that the erythrocyte receptor involved in enterotoxigenic *Escherichia coli* attachment is a sialoglycoconjugate J Clin. Microb. 21: 951–954 (1985).

10. Oro, H. S., et al., Identification of asialo GM1 as a binding structure for *Escherichia coli* colonization factor antigens., FEMS Microb. Lett. 72: 289–292 (1990).

11. Wenneras, C., et al., Binding of fibrillar CS3 adhesin of enterotoxigenic *Escherichia coli* to rabbit intestinal glycoproteins is competitively prevented by GalNAc(1–4)Gal containing glycoconjugates., Infec. Immun. 63: 640–646 (1995).

12. Schengrund et al "Binding of Vibrio cholera toxin and heat-labile enterotoxin of *Escherichia coli* to GM1, derivatives of GM1 and nonlipid oligosaccharide polyvalent ligands J. Biol. Chem. 264:13233–13237 (1989).

13. Fukuda et al "Comparison of the carbohydrate-binding specificities of cholera toxin and *Escherichia coli* heat-labile enterotoxins LTh-I, LTh-IIa, and LTh-IIb Infect. Immun. 56: 1748–1753 (1988).

14. Shida, K et al., *Escherichia coli* heat-labile enterotoxin binds to glycosylated proteins with lactose by aminocarbonyl reaction, Microbiol. Immunol. 38:273–279 (1994).

15. Sixma, T. K. et al., Lactose binding to heat-labile enterotoxin from *E. coli.*, Nature 355:561–564 (1992).

16. Merrit, E. A. et al., Galactose-binding site in *Escherichia coli* heat-labile enterotoxin (LT) and cholera toxin (CT), Mol. Microbiol. 13:745–753 (1994).

17. Uesaka et al., Simple method of purification of *Escherichia coli* heat-labile enterotoxin and cholera toxin using immobilized galactose Microb. Path. 16: 71–75 (1994).

18. Lemieux, R. U. et al., "The properties of a 'synthetic' antigen related to the blood-group Lewis A", J. Am. Chem. Soc., 97:4076–83 (1975).

19. Lemieux, R. U., et al., "Glycoside-Ether-Ester Compounds", U.S. Pat. No. 4,137,401, issued Jan. 30, 1979.

20. Lemieux, R. U., et al., "Artificial Oligosaccharide Antigenic Determinants", U.S. Pat. No. 4,238,473, issued Dec. 9, 1980.

21. Lemieux, R. U., et al., "Synthesis of 2-Amino-2-Deoxyglycoses and 2-Amino-2-Deoxyglycosides from glycals", U.S. Pat. No. 4,362,720, issued Dec. 7, 1982.

22. Cox, D., et al. "A New Synthesis of 4-0-α-D-Galactopyranosyl-D-Galacto-Pyranose", Carbohy. Res., 62: 245–252 (1978).

23. Dahmén, J., et al., "Synthesis of space arm, lipid, and ethyl glycosides of the trisaccharide portion [α-D-Gal-(1–4) -β-D-Gal(1–4)-β-D-Glc] of the blood group $p^k$ antigen: preparation of neoglycoproteins", Carbohydrate Research, 127: 15–25 (1984).

24. Garegg, P. J., et al., "A Synthesis of 8-Methoxycarbonyloct-1-yl O-α-D-Galactopyranosyl-(1–3) -0-β-D-Galactopyranosyl-(1–4)-2-Acetamido-2-Deoxy-β-D-Glucopyranoside", Carbohy. Res., 136: 207–213 (1985).

25. Garegg, P. J., et al., "Synthesis of 6- and 6'-deoxy derivatives of methyl 4-0-α-D-galactopyranosyl-β-D-galactopyranoside for studies of inhibition of pyelonephritogenic fimbriated *E. coli* adhesion to urinary epithelium-cell surfaces", Carbohy. Res., 137: 270–275 (1985).

26. Jacquinet, J. C., et al., "Synthesis of Blood-group Substances, Part 11. Synthesis of the Trisaccharide O-α-D-Galactopyranosyl-(1–3)-0-β-D-galactopyranosyl-(1–4)-2-acetamido-2-deoxy-D-glucopyranose", J. C. S. Perkin, I: 326–330 (1981).

27. Koike, K., et al., "Total Synthesis of Globotriaosyl-E and Z-Ceramides and Isoglobotriaosyl-E-Ceramide," Carbohydro. Res., 163: 189–208 (1987).

28. Schaubach, R., et al., "Tumor-Associated Antigen Synthesis: Synthesis of the Gal-α-(1–3)-Gal-β-(1–)-GlCNAc Epitope. A specific Determinant for Metastatic Progression?, " Liebigs Ann. Chem., 607–614 (1991).

29. Ratcliffe, R. M., et al., "Sialic Acid Glycosides, Antigens, Immunoadsorbents, and Methods for Their Preparation", U.S. Pat. No. 5,079,353, issued Jan. 7, 1992.

30. Okamoto, K., et al., "Glycosidation of Sialic Acid," Tetrahedron, 47: 5835–5857 (1990).

31. Abbas, S. A., et al., "Tumor-Associated Oligosaccharides I: Synthesis of Sialyl-Lewis' Antigenic Determinant", Sialic Acids, Proc. Japan-German Symp. Berlin 22–23 (1988).

32. Paulsen, "Advances in Selective Chemical Syntheses of Complex Oligosaccharides", Angew, Chem. Int. Ed. Eng., 21: 155–173 (1982).

33. Schmidt, "New Methods for the Synthesis of Glycosides and Oligosaccharides—Are There Alternatives to the Koenigs-Knorr Method?" Angew, Chem. Int. Ed. Eng., 25:212–235 (1986).

34. Fügedi, P., et al., "Thioglycosides as Glycosylating Agents in Oligosaccharide Synthesis", Glycoconjugate J., 4:97–108 (1987).

35. Kameyama, A., et al., "Total synthesis of sialyl Lewis X", Carbohydrate Res., 209; c1–c4 (1991).

36. Ekborg, G., et al., "Synthesis of Three Disaccharides for the Preparation of Immunogens bearing Immunodeterminants Known to Occur on Glycoproteins", Carbohydrate Research, 110: 55–67 (1982).

37. Dahmén, J., et al., "2-Bromoethyl glycosides: applications in the synthesis of spacer-arm glycosides," Carbohydrate Research, 118: 292–301 (1983).

38. Rana, S. S., et al., "Synthesis of Phenyl 2-Acetamido-2-Deoxy-3-O-α-L-Fucopyranosyl-β-D-Glucopyranoside and Related Compounds", Carbohydrate Research, 91: 149–157 (1981).

39. Amvam-Zollo, P., et al., "*Streptococcus pneumoniae* Type XIV Polysaccharide: Synthesis of a Repeating Branched Tetrasaccharide with Dioxa-Type Spacer-Arms", Carbohydrate Research, 150:199–212 (1986).

40. Paulsen, H., "Syntheses von oligosaccharid-determinanten mit amid-spacer vom typ des T-antigens", Carbohydr. Res., 104:195–219 (1982).

41. Chernyak, A. Y., et al., "A New Type of Carbohydrate-Containing Synthesis of Carbohydrate-Containing Synthetic Antigen: Polyacrylamide Copolymers having the Specificity of 0:3 and 0:4 Factors of Salmonella", Carbohydrate Research, 128: 269–282 (1984).

42. Fernandez-Santana, V., et al., "Glycosides of Monoallyl Diethylene Glycol. A New type of Spacer group of Synthetic Oligosaccharides", J. Carbohydrate Chemistry, 8(3), 531–537 (1989).

43. Lee, R. T., et al., "Synthesis of 3-(2-Aminoethylthio) PropylGlycosides", Carbohydrate Research, 37: 193–201 (1974).

44. Armstrong, G. D. et al., "Investigation of shiga-like toxin binding to chemically synthesized oligosaccharide sequences", J. Infec. Dis., 164:1160–7 (1991).

45. Heerze, L. D. et al., Oligosaccharide sequences attached to an inert support (SYNSORB) as potential therapy for antibiotic-associated diarrhea and pseudomembranous colitis, J. J. Infec. Dis., 169:1291–1296 (1994).

46. U.S. patent application Ser. No. 08/195,009, filed Feb. 14, 1994, by Heerze, et al., for TREATMENT OF ANTIBIOTIC ASSOCIATED DIARRHEA (now U.S. Pat. No. 5,484,773).

47. U.S. patent application Ser. No. 08/126,645, filed Sep. 27, 1993 by Armstrong, et al., for DIAGNOSIS AND TREATMENT OF BACTERIAL DYSENTERY.

48. U.S. patent application Ser. No. 07/996,913, filed Dec. 28, 1992, by Armstrong, for DIAGNOSIS AND TREATMENT OF BACTERIAL DYSENTERY.

The disclosure of the above publications, patents and patent applications are herein incorporated by reference in their entirety to the same extent as if the language of each individual publication, patent and patent application were specifically and individually included herein.

BACKGROUND OF THE INVENTION

Diarrhea is the most common health problem among travellers visiting less developed or tropical countries [1,2]. Although a number of enteropathogens have been implicated in traveller's diarrhea, and the most common microorganism associated with the disease is enterotoxigenic *Escherichia coli* (ETEC) which is responsible for over half of the reported cases [3]. ETEC isolates are also the causative agents for the majority of diarrheal cases in young children and infants in developing tropical countries [4]. In addition, diarrhea caused by ETEC is an important concern for military personnel when deployed to less developed countries [5,6].

ETEC isolates that cause diarrhea have several virulence factors that play important roles in the disease process. They include two enterotoxins, heat-labile toxin (LT) and heat-stable toxin (ST) and bacterial surface adhesins called pili which allow the organism to colonize the intestinal tract. Both toxins are not required to cause diarrhea. Some clinical ETEC isolates have been shown to produce either LT or ST, while other isolates have both toxins. Strains that possess LT tend to be associated with more severe cases of traveller's diarrhea, while ETEC strains that produce only ST cause milder diarrhea.

Of the three factors produced by ETEC that are implicated in causing diarrhea, two are mediated by a specific interaction with a cell surface oligosaccharide receptor. The enterotoxin LT utilizes the ganglioside GM1 ($\beta$Gal(1–3)$\beta$GalNAc(1–4)[$\alpha$NeuAc(2–3)]$\beta$Gal(1–4)$\beta$Glc-ceramide) to bind to host cells and induce diarrhea by stimulating adenylate cyclase activity [7,8]. Two types of pili are found in the outer membranes of ETEC. The most important type of pili associated with pathogenic *E. coli* strains are called colonization factor antigens (CFA) or coli surface antigens (CS) which are responsible for allowing the organism to colonize the intestinal mucosa. Several potential oligosaccharide receptors have been identified for CFA and include the asialo GM1 glycolipid structure ($\beta$Gal(1–3)$\beta$GalNAc(1–4)$\beta$Gal(1–4)$\beta$Glc-ceramide) as well as several sialic acid containing glycoconjugates [9,10]. In addition, the GalNAc(1–4)Gal disaccharide sequence has been shown to be a binding sequence for enterotoxigenic *E. coli* that express CS3 pili [11]. The other pili, type 1, are commonly found in *E. coli* strains, but do not appear to play a major role in causing diarrhea. Type 1 pili utilize mannose-containing oligosaccharide structures as a receptor. The other toxin associated with ETEC infections, ST, is a small polypeptide that interacts with its host cell receptor via a protein-protein interaction and induces diarrhea by increasing the levels of cyclic GMP in cells.

The current therapy for traveller's diarrhea is to initiate treatment with agents such as bismuth subsalicylate, Loperamide or agents such as Kaopectate in combination with rehydration therapy. The majority of the treatments involve the non-specific removal of the offending agents (i.e. toxins) from the intestinal tract. Only in moderate to severe cases of diarrhea where distressing or incapacitating symptoms are reported is antimicrobial therapy recommended. Antibiotics are not usually effective at reducing clinical symptoms of the disease and problems associated with antibiotic resistance can occur. A therapy is needed which would involve the specific removal of enterotoxigenic *E. coli* and/or LT activity from the intestine. This would lead to more rapid recovery and/or the lessening of symptoms in individuals who are suffering from diarrhea.

*E. coli* heat-labile enterotoxin (LT) has been found to display a lectin-like activity which allows it to bind to an oligosaccharide receptor on epithelial cells. Several oligosaccharide sequences have been identified as potential receptors for LT. Several glycolipids and their derivatives can serve as receptors for LT and include GM1 ($\beta$Gal(1–3)$\beta$GalNAc(1–4)[$\alpha$NeuAc(2–3)]$\beta$Gal(1–4)$\beta$Glc-ceramide).

Other gangliosides which have been shown to bind LT include [12,13] GD 1b (βGal(1–3)βGalNAc(1–4)[αNeuAc(2–3)αNeuAc(2–3)]βGal(1–4)βGlc-ceramide) and GM2 (βGalNAc(1–4)[αNeuAc(2–3)]βGal(1–4)βGlc-ceramide. Other derivatives of the ganglioside GM1 that were shown to bind LT include [12]:

βGal(1–3)βGalNH2(1–4)[αNeu-NH2(2–3)]βGal(1–4)βGlc-ceramide; βGal(1–3)βGalNAc(1–4)[αNeuAcR(2–3)]βGal(1–4)βGlc-ceramide, where R is the methyl ester of sialic acid; βGal(1–3)βGalNAc(1–4)[α(C7)NeuAc(2–3)]βGal(1–4)βGlc-ceramide; and βGal(1–3)βGalNAc(1–4)[αNeuAcR(2–3)]βGal(1–4)βGlc-ceramide, where R is ethanolamineamide.

In addition to glycolipid receptors, LT can utilize glycoproteins as receptors for toxin binding. LT has been shown to utilize glycoproteins that terminate in polylactosamine (βGal(1–4)βGlcNAc-) sequences [7]. LT also has the capability to bind to glycoproteins that terminate in lactose (βGal(1–4)βGlc)[14–16].

In addition, highly purified LT preparations have been obtained using galactose affinity columns [17].

In view of the above, there is a need for a compound which would treat traveller's diarrhea. A preferred compound would be administered noninvasively, such as orally, and would specifically remove toxin and/or organisms from the intestinal tract.

SUMMARY OF THE INVENTION

The invention provides compositions and methods for the treatment of traveller's diarrhea caused by enterotoxigenic E. coli.

The invention also provides compositions and methods for the treatment of traveller's diarrhea and associated symptoms caused by binding of enterotoxigenic E. coli to host cell oligosaccharide receptors in the gastrointestinal tract.

In one aspect, the invention provides a method to treat diarrhea mediated by LT in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds LT, and wherein said composition is capable of being eliminated from the gastrointestinal tract.

In a further aspect, the invention provides a pharmaceutical composition useful in treating traveller's diarrhea and related conditions initiated by LT, which composition comprises an oligosaccharide sequence covalently attached to a pharmaceutically acceptable solid, inert support through a non-peptidyl compatible linker arm, wherein said oligosaccharide sequence binds LT and a pharmaceutically acceptable carrier, wherein said composition is capable of being eliminated from the gastrointestinal tract.

In a still further aspect, the invention provides a method to treat traveller's diarrhea in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds enterotoxigenic E. coli and wherein said composition is capable of eliminating the microorganism from the gastrointestinal tract.

In yet a further aspect, the invention provides a pharmaceutical composition useful for treating traveller's diarrhea and related conditions initiated by enterotoxigenic E. coli, which composition comprises an oligosaccharide sequence covalently attached to a pharmaceutically acceptable solid, inert support through a non-peptidyl compatible linker arm, wherein said oligosaccharide sequence binds enterotoxigenic E. coli; and a pharmaceutically acceptable carrier, wherein said composition is capable of eliminating the microorganism from the gastrointestinal tract.

In a further aspect still, the invention provides a method to bind and remove LT and/or enterotoxigenic E. coli from a sample suspected of containing said toxin and/or organism, which method comprises contacting said sample with an oligosaccharide sequence covalently attached to a solid, inert support through a non-peptidyl compatible linker arm, wherein said oligosaccharide sequence binds LT and/or enterotoxigenic E. coli, under conditions wherein said toxin and/or organism is absorbed to said support; and separating the support containing the absorbed toxin and/or organisms from the sample.

DETAILED DESCRIPTION OF THE INVENTION

A. Definitions

As used herein the following terms have the following meanings:

The term "traveller's diarrhea" refers to diarrhea of sudden onset, often accompanied by abdominal cramps, vomiting and fever that occurs sporadically in traveller's, usually during the first week of a trip. This diarrhea is most commonly caused by enterotoxigenic E. coli.

The term "biocompatible" refers to chemical inertness with respect to human tissues or body fluids. Biocompatible materials are non-sensitizing.

The term "compatible linker arm" refers to a moiety which serves to space the oligosaccharide structure from the biocompatible solid support and which is bifunctional wherein one functional group is capable of binding to a reciprocal functional group of the support and the other functional group is capable of binding to a reciprocal functional group of the oligosaccharide structure. Compatible linker arms preferred in the present invention are non-peptidyl spacer arms.

The term "solid support" refers to an inert, solid material to which the oligosaccharide sequences may be bound via a compatible linker arm. Where use is in vivo, the solid support will be biocompatible.

The term "SYNSORB" refers to synthetic 8-methoxycarbonyloctyl oligosaccharide structures covalently coupled to Chromosorb P™ (Manville Corp., Denver, Colo.) [18], which is a derivatized silica particle.

The terms "heat-labile toxin" or "LT" refer to an enterotoxin of enterotoxigenic E. coli which initiates traveller's diarrhea and related conditions. This toxin has a lectin-like activity.

For purpose of this application, all sugars are referenced using conventional three letter nomenclature. All sugars are assumed to be in the D-form unless otherwise noted, except for fucose, which is in the L-form. Further all sugars are in the pyranose form.

B. Synthesis

Chemical methods for the synthesis of oligosaccharide structures can be accomplished by methods known in the art. These materials are generally assembled using suitably protected individual monosaccharides.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [19–35].

The solid supports to which the oligosaccharide structures of the present invention are bound may be in the form of sheets or particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Solid supports made of inorganic materials are preferred. Preferably the solid supports have a particle size of from about 10 to 500 microns for in vivo use. In particular, particle sizes of 100 to 200 microns are preferred.

The oligosaccharide structure(s) is covalently bound or noncovalently (passively) adsorbed onto the solid support. The covalent bonding may be via reaction between functional groups on the support and the compatible linker arm of the oligosaccharide structure. It has unexpectedly been found that attachment of the oligosaccharide structure to the biocompatible solid support through a compatible linking arm provides a product which, notwithstanding the solid support, effectively removes toxin. Linking moieties that are used in indirect bonding are preferably organic bifunctional molecules of appropriate length (at least one carbon atom) which serve simply to distance the oligosaccharide structure from the surface of the solid support.

The compositions of this invention are preferably represented by the formula:

(OLIGOSACCHARIDE-Y—R)$_n$- SOLID SUPPORT where OLIGOSACCHARIDE represents an oligosaccharide group of at least 2 sugar units which group binds to LT and/or enterotoxigenic E. coli, Y is oxygen, sulfur or nitrogen, R is an aglycon linking arm of at least 1 carbon atom, SOLID SUPPORT is as defined above, and n is an integer greater than or equal to 1. R is preferably an aglycon of from 1 to about 10 carbon atoms. Oligosaccharide sequences containing about 1 to 10 saccharide units may be used. Sequences with about 1 to 3 saccharide units are preferred. Preferably, n is an integer such that the composition contains about 0.25 to 2.50 micromoles oligosaccharide per gram of composition.

Numerous aglycon linking arms are known in the art. For example, a linking arm comprising a para-nitrophenyl group (i.e., —OC$_6$H$_4$pNO$_2$) has been disclosed [36]. At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed [37]. Specifically, the linking arm is derived from a 2-bromoethyl group which, in a substitution reaction with thionucleophiles, has been shown to lead to linking arms possessing a variety of terminal functional groups such as —OCH$_2$CH$_2$SCH$_2$CO$_2$CH$_3$ and —OCH$_2$CH$_2$SC$_6$H$_4$-pNH$_2$. These terminal functional groups permit reaction to complementary functional groups on the solid support, thereby forming a covalent linkage to the solid support. Such reactions are well known in the art.

A 6-trifluoroacetamido-hexyl linking arm (—O—(CH$_2$)$_6$—NHCOCF$_3$) has been disclosed [38] in which the trifluoroacetamido protecting group can be removed, unmasking the primary amino group used for coupling.

Other exemplifications of known linking arms include the 7-methoxycarbonyl-3,6,dioxaheptyl linking arm [39] (—OCH$_2$—CH$_2$)$_2$OCH$_2$CO$_2$CH$_3$); the 2-(4-methoxycarbonylbutancarboxamido)ethyl [40] (—OCH$_2$CH$_2$NHC(O)(CH$_2$)$_4$CO$_2$CH$_3$); the allyl linking arm [41] (—OCH$_2$CH=CH$_2$) which, by radical co-polymerization with an appropriate monomer, leads to co-polymers; other allyl linking arms [42] are known (—O(CH$_2$CH$_2$O)$_2$CH$_2$CH=CH$_2$). Additionally, allyl linking arms can be derivatized in the presence of 2-aminoethanethiol [43] to provide for a linking arm $—OCH_2CH_2CH_2SCH_2CH_2NH_2$. Other suitable linking arms have also been disclosed [19–21,23,24].

The particular linking employed to covalently attach the oligosaccharide group to the solid support is not critical.

Preferably, the aglycon linking arm is a hydrophobic group and most preferably, the aglycon linking arm is a hydrophobic group selected from the group consisting of $—(CH_2)_8C(O)—$, $—(CH_2)_5OCH_2CH_2CH_2—$ and $—(CH_2)_8CH_2O—$.

We have found that synthetic oligosaccharide sequences covalently attached to a biocompatible solid support, e.g., Chromosorb P™ (SYNSORB) may be used to bind LT. These compositions are useful to treat traveller's diarrhea. SYNSORB is particularly preferred for these compositions because it is non-toxic and resistant to mechanical and chemical deposition. In studies using rats (a widely accepted model for preclinical studies, since they are predictive of human response), SYNSORBs have been found to pass unaffected through the rat gastrointestinal tract. They were found to be eliminated completely and rapidly (99% eliminated in 72 hours) following oral administration.

Figure 3:
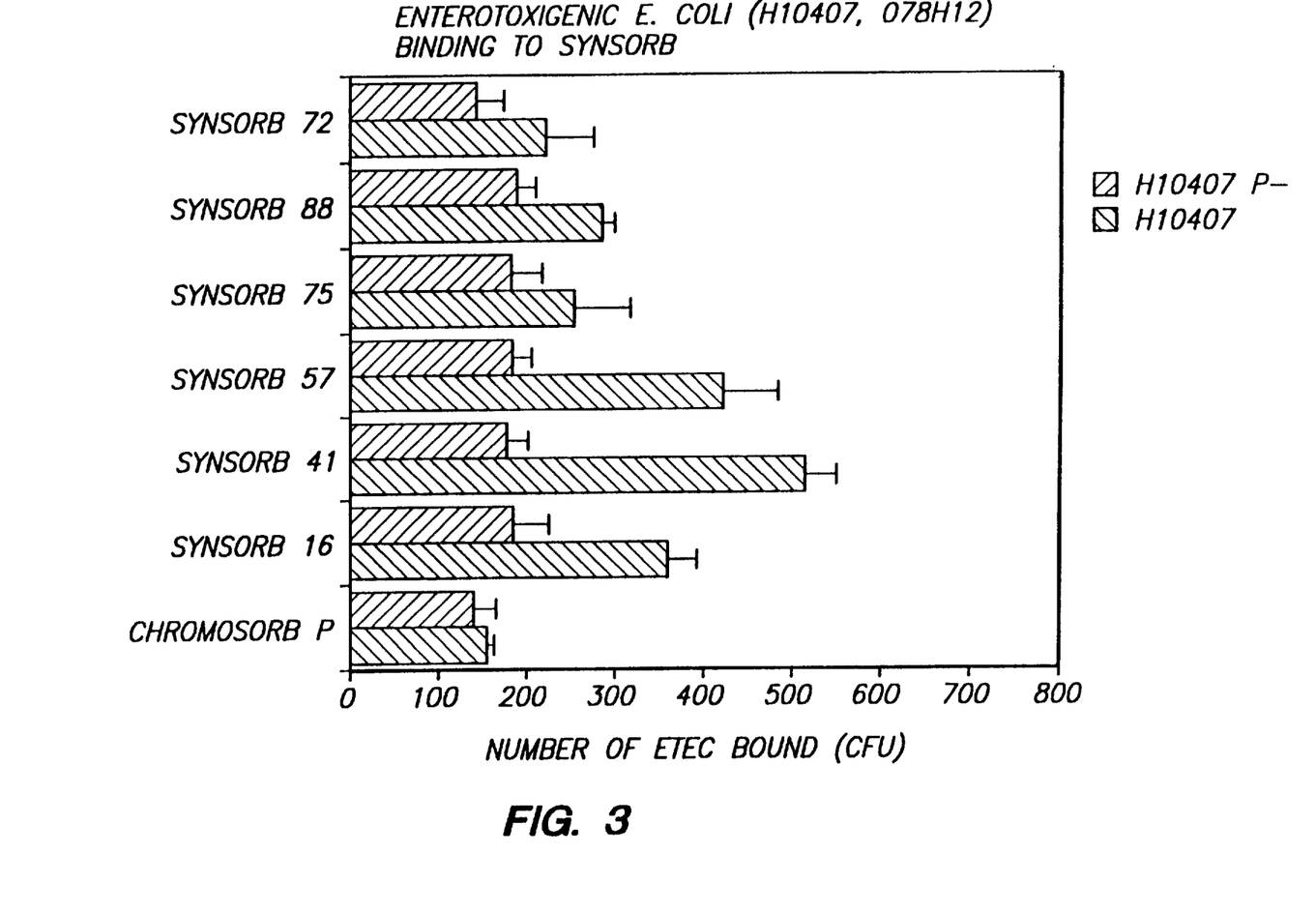
FIG. 3 demonstrates the effectiveness of SYNSORB binding to E. coli H10407 (O78H12) and H10407P-. The results show that H10407 can colonize the surface of SYNSORBs 16, 41, 57 and 88. The results also show that E. coli binding to SYNSORB is mediated by CFA pili as demonstrated by the inability of H10407P- to bind significantly better to SYNSORB than to Chromosorb P.
Figure 4:
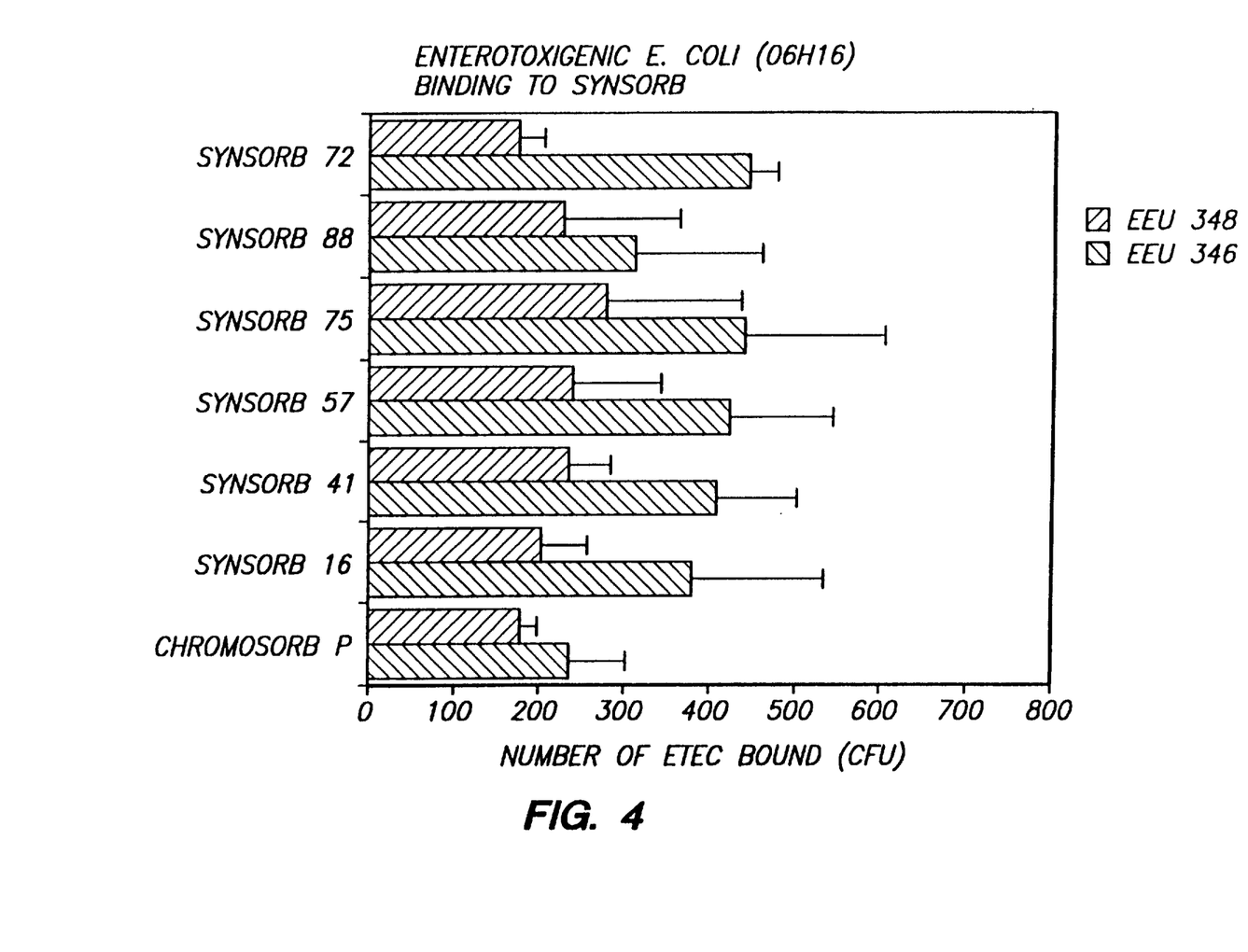
FIG. 4 demonstrates the effectiveness of SYNSORB binding to two isolates to enterotoxigenic E. coli (O6H16). The results show that O6 serotypes of E. coli bind to several SYNSORBs tested.
Figure 5:
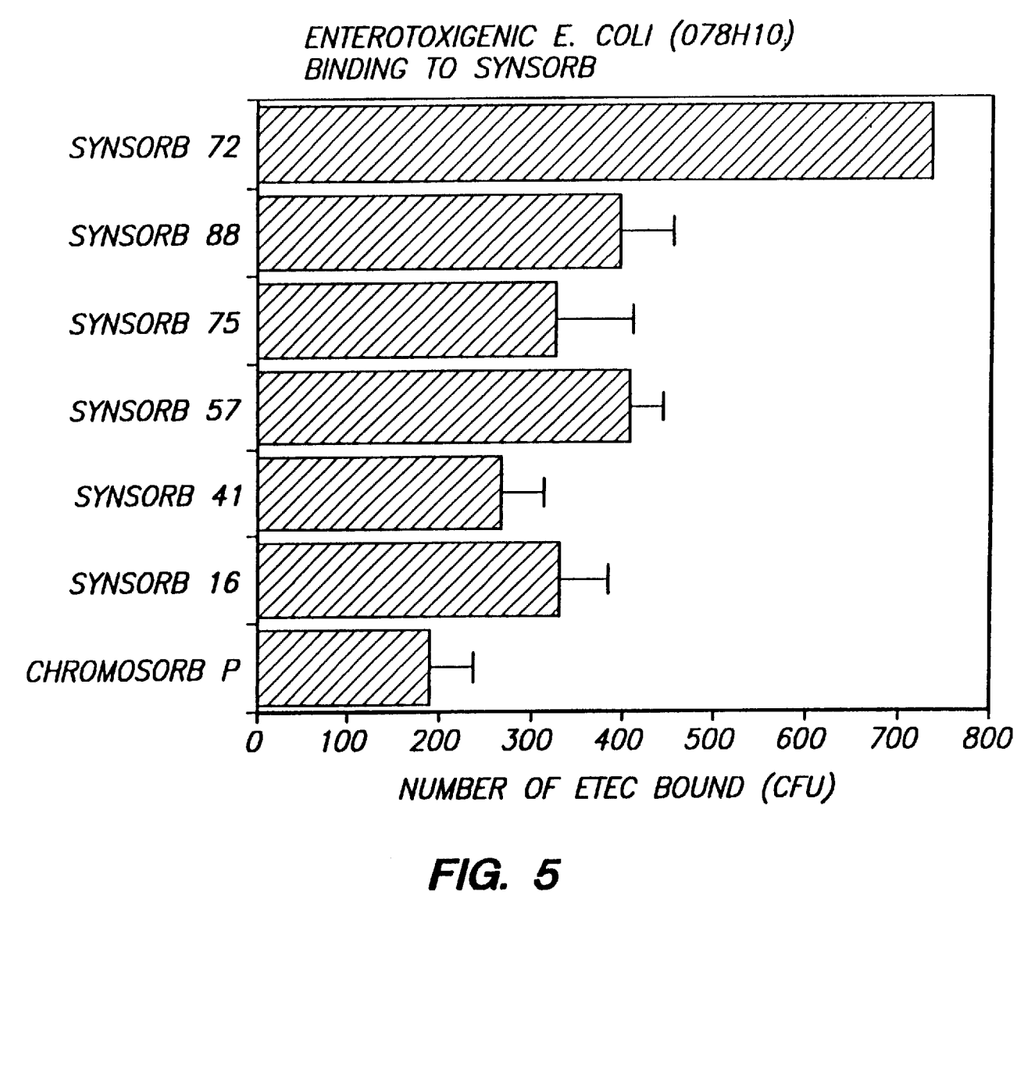
FIG. 5 demonstrates the effectiveness of SYNSORB binding to enterotoxigenic E. coli (O78H10) The results show that O78H10 serotypes of E. coli bind to several SYNSORBs tested.

Additionally, the high density of oligosaccharide moieties on SYNSORB is particularly useful for binding LT, since the toxin is thought to possess multiple oligosaccharide binding sites [15]. The high density of oligosaccharide ligands on SYNSORB is also useful for binding large numbers of enterotoxigenic *E. coli.*

Non-peptidyl linking arms are preferred for use as the compatible linking arms of the present invention. The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable due to, for example, questionable stability in the gastrointestinal tract when given orally.

Covalent attachment of an oligosaccharide group containing an LT or enterotoxigenic *E. coli* binding unit through a non-peptidyl spacer arm to an inert solid support permits efficient binding and removal of LT and/or microorganism from a sample to be analyzed for the presence of LT and/or enterotoxigenic *E. coli* from the intestine of a patient suffering from traveller's diarrhea. When the oligosaccharide is synthesized with this compatible linker arm attached (in non-derivatized form), highly pure compositions may be achieved which can be coupled to various solid supports.

C. Pharmaceutical Compositions

The methods of this invention are achieved by using pharmaceutical compositions comprising one or more oligosaccharide structures which bind LT and/or enterotoxigenic *E. coli* attached to a solid support.

When used for oral administration, which is preferred, these compositions may be formulated in a variety of ways. It will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art.

Compositions which may be mixed with semisolid foods such as applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The SYNSORB itself may also be used without the addition of inert pharmaceutical carriers, particularly for use in capsule form.

Doses are selected to provide neutralization of LT and elimination of toxin and/or enterotoxigenic *E. coli* from the gut of the affected patient. Preferred doses are from about 0.25 to 1.25 micromoles of oligosaccharide/kg body weight/day, more preferably about 0.5 to 1.0 micromoles of oligosaccharide/kg body weight/day. Using SYNSORB compositions, this means about 0.5 to 1.0 gram SYNSORB/kg body weight/day, which gives a concentration of SYNSORB in the gut of about 20 mg/ml. Administration is expected to be 3 or 4 times daily, for a period of one week or until clinical symptoms are resolved. The dose level and schedule of administration may vary depending on the particular oligosaccharide structure used and such factors as the age and condition of the subject. Optimal time for complete removal of LT activity was found to be about 1 hour at 37° C., using a concentration of SYNSORB of 20 mg in 1 ml sample. Similar conditions can be used to effectively remove enterotoxigenic *E. coli* from the gut.

Administration of the oligosaccharide-containing compositions of the present invention during a period of up to seven days will be useful in treating traveller's diarrhea. Also, prophylactic administration will be useful to prevent colonization of the gut by enterotoxigenic *E. coli* and subsequent development of the disease.

As discussed previously, oral administration is preferred, but formulations may also be considered for other means of administration such as per rectum. The usefulness of these formulations may depend on the particular composition used and the particular subject receiving the treatment. The formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 1 micromole oligosaccharide/ml.

D. Methodology

We have found that *E. coli* heat-labile toxin (LT) may be neutralized by certain oligosaccharide sequences which bind the toxin. In particular, synthetic oligosaccharides covalently attached to solid supports via non-peptidyl compatible linker arms have been found to neutralize LT effectively. Examples of such compositions are certain SYNSORBs, which bind and neutralize LT activity.

We have also found that enterotoxigenic *E. coli* can bind to certain oligosaccharide sequences that are covalently attached to solid supports via non-peptidyl compatible linker arms. Examples of such compositions are certain SYNSORBs which bind to enterotoxigenic *E. coli* and prevent the organism from attaching to host cell receptors in the intestinal tract.

We have tested the ability of several oligosaccharide sequences attached to Chromosorb P via an 8-methoxycarbonyloctyl (MCO) spacer arm to neutralize LT and bind enterotoxigenic *E. coli.* The structures tested, also referred to as SYNSORBs, are presented in Table 1. As shown in FIGS. 1 and 2 and Table 2, the SYNSORBs tested varied in their ability to neutralize at least about 50% of the LT activity. FIGS. 3–5 demonstrate the ability of SYNSORB to bind enterotoxigenic *E. coli*.

The oligosaccharide sequences attached to solid supports useful in the present invention include those which bind LT. The binding affinity of an oligosaccharide to LT is readily detectable by a simple in vitro test, as for example, set forth in Example 1 below. For the purposes of this invention, oligosaccharide sequences attached to solid supports which bind LT means those compositions which reduce cytotoxicity in Chinese Hamster Ovary (CHO) cell assays by at least 50%, using the assay set forth in the Examples section.

Other oligosaccharide sequences attached to solid supports useful in this present invention are those which can bind enterotoxigenic *E. coli*. significantly better ($p \leq 0.05$, using appropriate standard statistical methods, such as Wilcoxon or Student's T-test) than a control support that does not contain any attached oligosaccharide sequences (Chromosorb P). The binding affinity of an oligosaccharide for enterotoxigenic *E. coli* is determined as outlined in Example 4 below.

The binding of shiga-like toxins (SLTs) and toxin a produced by *Clostridium difficile* to chemically synthesized oligosaccharide sequences has been studied [44–48].

SLTs are a group of cytotoxins which are made up of two parts: an A subunit and a B oligomer. The oligomer is the binding portion of the toxin that allows it to bind to host cell receptors. The SLT toxins bind to glycolipid receptors containing the αGal(1–4)βGal determinant. The A subunit has an enzymatic activity (N-glycosidase) that depurinates 28S ribosomal RNA in mammalian cells. This enzymatic activity abolishes the ability of the toxin-infected cell to perform protein synthesis.

The site for SLT action is endothelial cells found in the kidneys and mesenteric vasculature, and SLTs may cause damage that can result in renal failure and hemoglobin in the urine. SLTs are the causative agent in the hemolytic-uremic syndrome. SLTs may also be partially involved in the pathogenesis of hemorrhagic colitis (bloody diarrhea).

Toxin A produced by *Clostridium difficile* is an enterotoxin that induces fluid secretion, mucosal damage and intestinal inflammation. It serves as a chemoattractant for human neutrophils. Toxin A is a single protein. It causes activation and results in the release of cytokines in monocytes. These inflammatory effects may play an important role in inducing the colonic inflammation seen in pseudomembranous colitis.

Toxin A appears to bind to a glycoprotein receptor, the structure of which has yet to be determined. The mechanism of action is not totally understood, but toxin A is thought to enter cells via receptor-mediated endocytosis and affect the actin cytoskeleton of the cell. The toxin A receptor is thought to be linked to a guanine regulatory protein. Toxin A is the first step in the production of *C. difficile*-associated diarrhea and pseudomembranous colitis.

In contrast, *E. coli* heat-labile toxin (LT) is a heterohexamer composed of an A subunit which as latent ADP-ribosyltransferase activity and a pentameric B subunit which recognizes receptor sites [1]. When taken into the cell, the A subunit is metabolized via proteolytic cleavage and subsequent reduction to the $A_1$ peptide. The $A_1$ peptide activates adenylyl cyclase, causing elevated intracellular cyclic AMP levels. This leads to loss of water and electrolytes into the lumen of the intestine, and diarrhea.

LT has the ability to utilize both glycoprotein as well as glycolipid receptors. The major receptor for LT is the ganglioside GM1, but LT also recognizes glycoproteins with oligosaccharide structures that terminate in the βGal(1–4)βGlcNAc sequence [3,7,13]. LT also has the capability to bind the glycoproteins that terminate in lactose (βGal(1–4)βGlc) [14–16].

Previous studies defining the oligosaccharide binding specificity of LT have identified several structural requirements for toxin binding [13]. Oligosaccharides which terminate in the βGal(1–3)βGalNAc(1–4)[αNeuAc(2–3)]βGal sequences have been shown to be important for binding. In addition, LT also recognizes the GM2 ganglioside (βGalNAc(1–4)[αNeuAc(2–3) βGal(1–4)βGlc-ceramide) as well as the asialo GM1 glycolipid (βGal(1–3)βGalNAc(1–4)βGal(1–4)βGlc-ceramide [13]. The minimum requirement for LT binding appears to be a terminal galactose saccharide [17]. The SYNSORBs chosen for toxin neutralization studies include carbohydrates that incorporate selected structural features of the GM1 structure as well as other oligosaccharides not known to bind to LT.

Utilizing purified LT, a panel of SYNSORBs (Table 1) containing a variety of oligosaccharide structures was screened for the ability to adsorb toxin activity. The extent of LT neutralization was determined by measuring the reduction in the end point titres in the CHO cell assay of toxin solutions that had been incubated with SYNSORB relative to untreated control samples. The results from initial screening experiments (FIG. 1) showed that SYNSORBs 16, 19, 41, 72, 75 and 88 containing the oligosaccharide sequences βGal(1–4)βGlc (SYNSORB 16), βGal (SYNSORB 19), βGal(1–3)βGalNAc (SYNSORB 41), βGal(1–3)βGal (SYNSORB 72), βGal(1–3)βGalNAc(1–4)βGalNAc(1–4)βGal (SYNSORB 75) or αNeuAc(2–3) βGal (SYNSORB 88) were found to neutralize purified LT activity by 96%, 80%, 96%, 98%, 99% and 96% (n=2), respectively, at a concentration of 20 mg/ml. SYNSORB 57 failed to adsorb toxin activity. The results in FIG. 1 also show that Chromosorb P does not appear to bind to LT.

Other oligosaccharide sequences which are also useful in the present invention are those comprising a terminal βGal(1–3)βGal(1–4)βGal(1) moiety.

Figure 2:
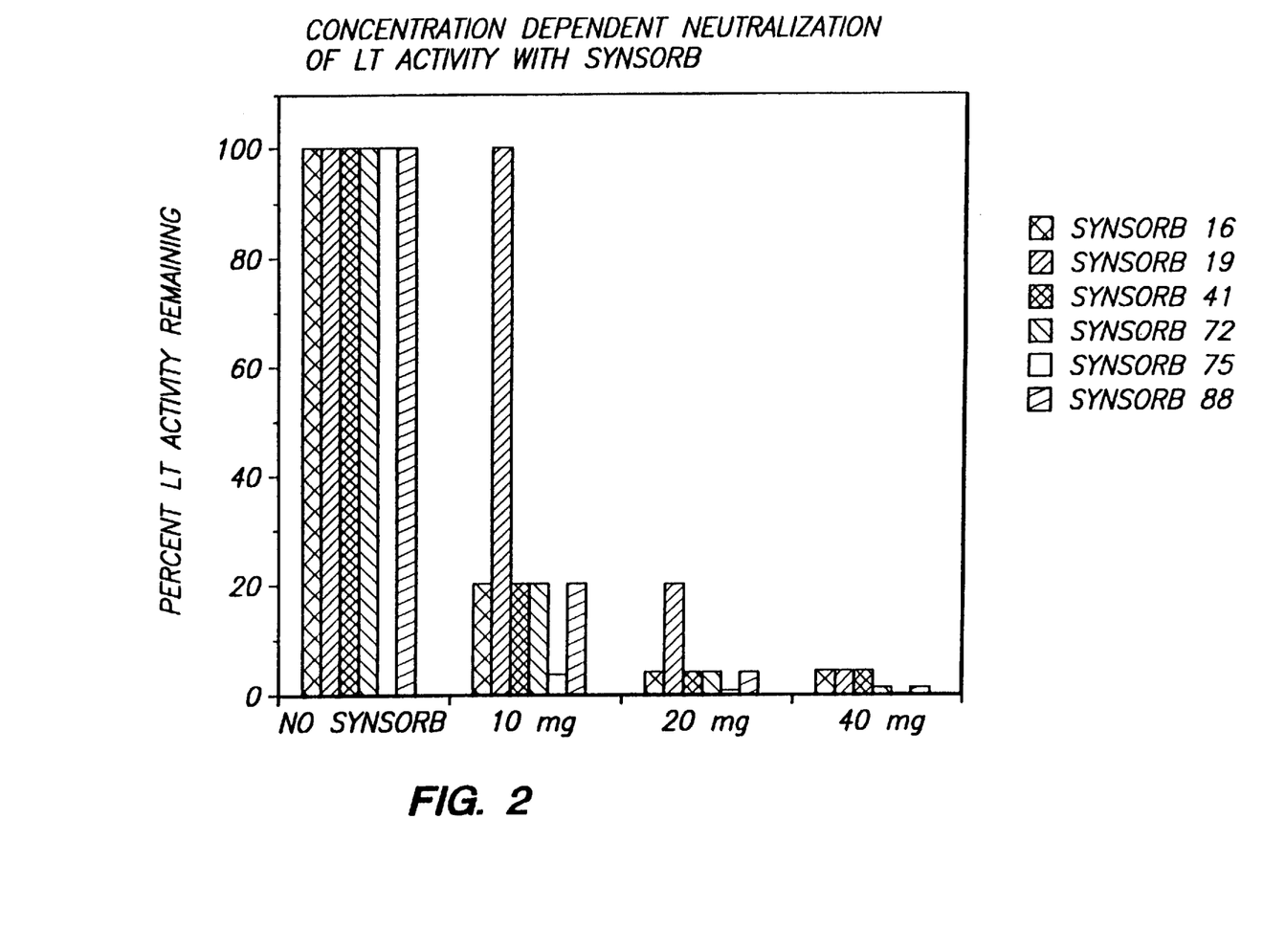
FIG. 2 illustrates the concentration dependent neutralization of LT activity using SYNSORB 16, 19, 41, 72, 75 and 88. All SYNSORBs tested can effectively neutralize more than about 75% LT cytotonicity at concentrations of 20 mg/ml or greater.

The capacity of SYNSORBs 16, 19, 41, 72, 75 and 88 adsorb LT activity was determined by incubating variable amounts of SYNSORB with LT. The results in FIG. 2 show that these SYNSORBs used at a concentration of 20 mg/ml for 1 hour at room temperature can effectively neutralize greater than 95% of toxin activity.

Once optimal binding conditions were determined for SYNSORBs 16, 41, 75, and 88, these conditions were used to neutralize LT activity from polymyxin extracts of clinical isolates of enterotoxigenic *E. coli*. The results in Table 2 indicate that SYNSORB has the ability to effectively adsorb toxin activity regardless of ETEC strain, although the relative affinities for each SYNSORB varied between strains, indicating that the LT produced by each isolate may be slightly different.

Thus, we have found that the ability to neutralize LT is directly related to the oligosaccharide sequences attached to the inert support.

Several different oligosaccharide sequences attached to solid supports via compatible linker arms have been found to have the ability to neutralize LT activity. These sequences, and others that also bind LT, may be used to treat traveller's diarrhea. Optimal time for complete removal of LT activity was found to be about 1 hour at 37° C, using a concentration of SYNSORB of 20 mg in 1 ml sample. Since each gram of SYNSORB contains approximately 0.25 to 1.0 micromoles oligosaccharide, the total amount of oligosaccharide to be given in a daily dose would range from 7.5 to 30 micromoles, using a gut volume of four liters.

Treatment of traveller's diarrhea may be accomplished by oral administration of compositions containing oligosaccharide sequences covalently bound to a solid support via a compatible linker arm (e.g. SYNSORBs). For example, the SYNSORB has been found to pass through the stomach of rats intact. It then contacts the LT in the intestinal tract. Subsequent elimination of the intact SYNSORB with LT bound to its results in elimination of LT from the patient.

The primary virulence factor responsible for attachment of enterotoxigenic E. coli to epithelial cells in the intestine are the colonization factor antigen (CFA) pili. Several potential oligosaccharide receptors have been identified for CFA and include the asialo GM1 glycolipid structure ($\beta$Gal(1–3) $\beta$GalNAc(1–4)$\beta$Gal(1–4)$\beta$Glc-ceramide) as well as several sialic acid containing glycoconjugates [9,10]. Since CFA pili utilize similar oligosaccharides (glycolipids) for binding as LT, the SYNSORBs chosen (Table 1) for bacterial attachment studies include carbohydrates that correspond to selected sequences found within the GM1 ganglioside structure to prevent colonization of enterotoxigenic E. coli.

The amount of enterotoxigenic E. coli binding to the surface of SYNSORB was determined by plating suspensions of SYNSORB that had been incubated with a culture of enterotoxigenic E. coli ($1 \times 10^5$ colony forming units (CFU)/ml). Control incubations were done with enterotoxigenic E. coli and Chromosorb P, which does not contain any attached oligosaccharide sequences. An additional control suing an E. coli isolate (EEU 351, H10407 P-) that does not express CFA pili was included to demonstrate that the binding of enterotoxigenic E. coli to the surface of SYNSORB was mediated by pili. The results in FIGS. 3–5 show that SYNSORBs 16, 41, 57, 72, 75 and 88 can serve as binding sites for one or more serotypes of enterotoxigenic E. coli. All six of these SYNSORBs contain oligosaccharide sequences that have not been previously shown to bind to enterotoxigenic E. coli.

Thus, we have found that the ability to bind enterotoxigenic E. coli is directly related to the oligosaccharide sequences attached to the inert support. The results in FIGS. 3–5 show the importance of the $\beta$Gal(1–4)$\beta$Glc, $\beta$Gal(1–3) GalNAc, $\beta$GalNAc(1–4)$\beta$Gal or $\alpha$NeuAc(2–3)$\beta$Gal linkages for enterotoxigenic E. coli binding. In addition, we have found that oligosaccharides that possess $\beta$Gal(1–3) $\beta$Gal sequences can also effectively bind enterotoxigenic E. coli. Accordingly, oligosaccharide sequences comprising $\beta$Gal(1–4)$\beta$Gal(2) will be useful in the methods and compositions of the present invention.

Treatment of traveller's diarrhea or related conditions may be accomplished by oral administration of compositions containing oligosaccharide sequences covalently bound to a solid support via a compatible linker arm (e.g. SYNSORBs). For example, the SYNSORB has been found to pass through the stomach of rats intact. It then contacts the enterotoxigenic E. coli organisms in the intestinal tract. Subsequent elimination of the intact SYNSORB with enterotoxigenic E. coli bound to it results in elimination of the organism from the patient. This form of SYNSORB treatment is highly desirable in cases of traveller's diarrhea where the enterotoxigenic E. coli strain responsible for the disease does not produce any LT.

Another aspect of the invention is the rapid efficient binding of physiological concentrations of LT and/or enterotoxigenic E. coli present in biological samples, thus permitting assay of the presence and/or quantity of LT and/or organism in these samples. Typically, the biological sample will be a stool sample. The sample may be extracted and prepared using standard extraction techniques. The sample or extract is then contacted with the toxin-binding oligosaccharide sequences covalently bound to solid supports via a compatible linker arm under conditions where any LT in the sample is absorbed.

The heat-labile toxin (LT) and/or enterotoxigenic E. coli may be measured directly on the surface of the oligosaccharide-containing support using any suitable detection system. For example, radioactive, biotinylated or fluorescently labelled monoclonal or polyclonal antibodies specific for LT may be used to determine the amount of LT bound to the support. A wide variety of protocols for detection of formation of specific binding complexes analogous to standard immunoassay techniques is well known in the art.

E. Examples

The following methods were used to perform the studies in the Examples that follow.

Purified LT was obtained from Sigma Chemicals.

Preparation of Crude LT Extracts of Enterotoxigenic E. coli Clinical Isolates

Enterotoxigenic E. coli were grown overnight at 37° C. on CFA agar plates. A polymyxin extract of E. coli was prepared by suspending the bacteria in 1 ml of phosphate buffered saline (PBS) containing 0.1 mg of polymyxin B sulfate. After incubating the mixture for 30 min, the extracts were centrifuged at 14,000 rpm for 10 min in an Eppendorf microcentrifuge. The resulting supernatant was removed and used in SYNSORB neutralization experiments.

Assay of Heat Labile Enterotoxin (LT) Activity Using Tissue Culture Cells

The cytotonic activity of LT can be measured by the use of Chinese hamster ovary cells (CHO) that were maintained in Hams f12 media supplemented with 10% fetal bovine serum (FBS) in an atmosphere of 5% $CO_2$ at 37° C. LT samples to be tested were diluted 1:5 in Hams media and filter sterilized through 0.22 micron syringe filters. Samples to be tested were serial 5-fold diluted in media and 100 $\mu$L of each dilution was added wells with confluent monolayers of CHO cells and incubated for 24 h at 37° C./5% $CO_2$. Each sample was analyzed two times. Cytotonic effects are readily visible after 24 h incubation by comparing wells with controls that do not contain toxin. After 24 h, the cells were fixed with 95% methanol and stained with Geimsa stain. LT containing samples from neutralization experiments were treated in an analogous fashion except that the percent neutralization was determined by comparing the endpoint dilutions of samples with and without SYNSORB.

Another cell line used to measure the effects of LT is the human colonic adenocarcinoma HT 29 cell line. These cells were grown in the presence of 17 mM glucose using Dulbecco's Modified Eagles Medium (DMEM) plus 10% fetal bovine serum. LT containing solutions were serial 3 or 5-fold in media and added to wells containing HT 29 cells. Pleomorphic vacuole formation was readily visible after 24 h incubation by comparing wells with controls that did not contain any toxin.

The following examples are offered to illustrate this invention and are not meant to be construed in any way as limiting the scope of this invention.

EXAMPLE 1

Screening of Oligosaccharide-containing Solid Supports for the Ability to Neutralize LT Activity A solution containing purified LT (2 $\mu$g in 1 ml PBS) was added to various SYNSORBs (amounts ranging from 17.8 to 20.7 mg) containing different oligosaccharide sequences in 1.5 ml microcentrifuge tubes and incubated at room temperature for 1 h on a end-over-end rotator. After incubation, the SYNSORB was allowed to settle to the bottom of the tubes and the supernatants were carefully removed. Serial five-fold dilutions of the supernatants were prepared and the cytotonic endpoint determined as described above. The extent of reduction in the endpoint of the presence of SYNSORB was determined by comparing with controls in which SYNSORB was not added. An additional control utilized was Chromosorb which is void of any carbohydrate ligand.

Figure 1:
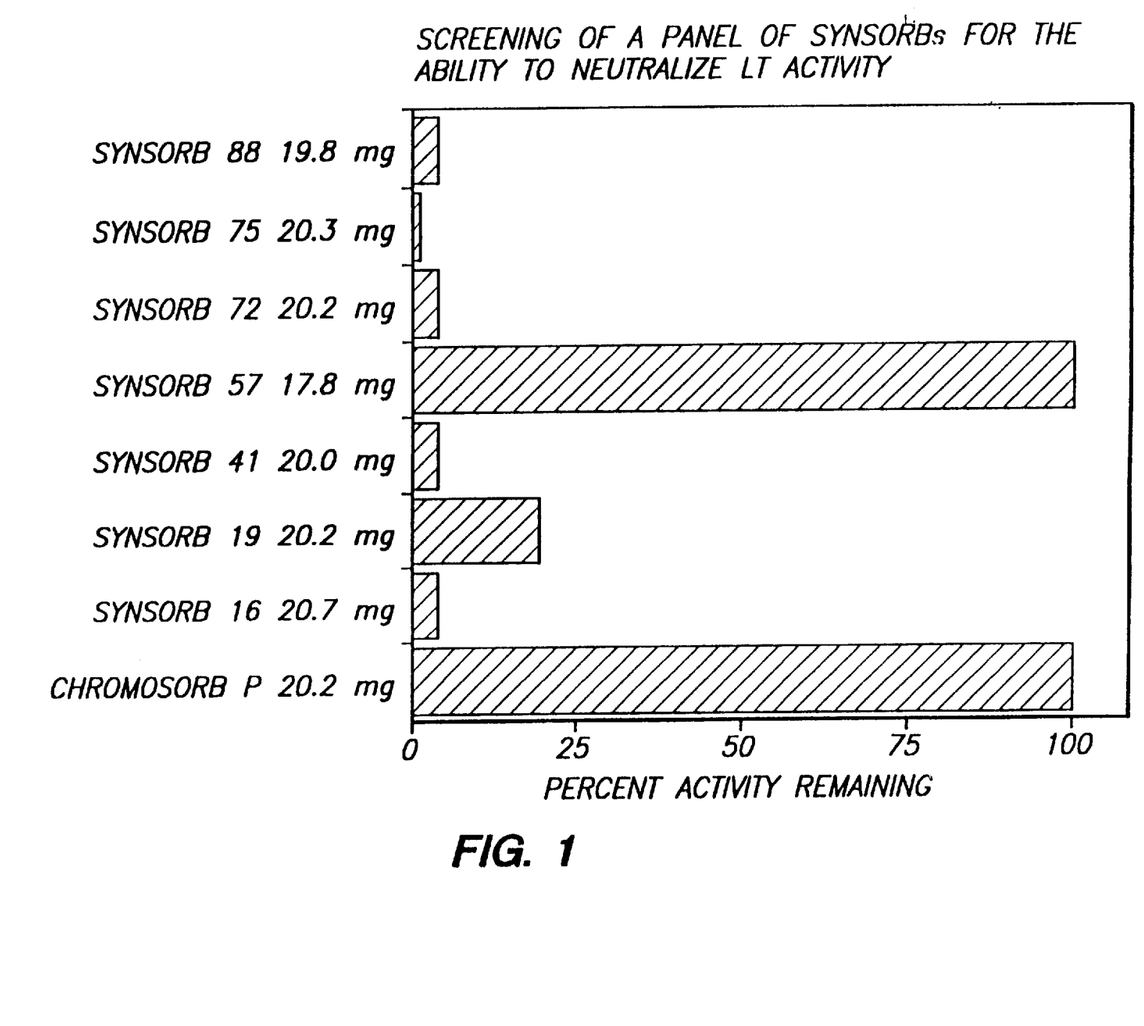
FIG. 1 demonstrates the neutralization of purified heat-labile toxin (LT) cytotonicity using a panel of SYNSORBs containing various oligosaccharide sequences. Several SYNSORBs were found to effectively neutralize LT activity.

Results are shown in FIG. 1, and demonstrate that several oligosaccharide structures were found to effectively neutralize LT activity.

EXAMPLE 2

Concentration Dependent Neutralization of LT Activity Using SYNSORB 16, 19, 41, 72, 75 and 88

The amount of SYNSORBs 16, 19, 41, 72, 75 and 88 required for maximal LT neutralization was determined by adding 1 ml of a purified LT solution containing 2 μg LT to pre-weighed amounts of each SYNSORB in 1.5 ml microcentrifuge tubes. SYNSORB samples were tested using 10, 20 and 40 mg amounts. Samples were incubated for 1 hour at 37 C. on an end-over-end rotator. Control samples containing only LT were also tested.

The amount of neutralization in each sample was determined by comparing the endpoint titers of CHO cell assays from samples with an without SYNSORB. The results, shown in FIG. 2, demonstrate that about 20 mg of each SYNSORB tested was able to neutralize at lease 75% of the LT activity in solution.

EXAMPLE 3

Screening of Oligosaccharide-containing Solid Supports for the Ability to Neutralize LT from Clinical Isolates of Enterotoxigenic E. coli Polymyxin extracts from clinical isolates of enterotoxigenic E. coli (1 ml) were added to various SYNSORBs (amounts ranging from 20.0 to 22.5 mg) containing different oligosaccharide sequences in 1.5 ml microcentrifuge tubes and incubated at room temperature for 1 h on a end-over-end rotator. After incubation, the SYNSORB was allowed to settle to the bottom of the tubes and the supernatants were carefully removed. Serial three or five-fold dilutions of the supernatants were prepared and the cytotonic or cytotoxic endpoints determined as described above. The extent of reduction in the endpoint in the presence of SYNSORB was determined by comparing with controls in which SYNSORB was not added. An additional control utilized was Chromosorb which is void of any carbohydrate ligand.

The results shown in Table 2 demonstrate the neutralization of crude LT activity from polymyxin extracts of enterotoxigenic E. coli using SYNSORBs at a concentration of 20 mg/ml. The results in Table 2 indicate that several oligosaccharide structures were found to effectively neutralize LT activity.

EXAMPLE 4

Binding experiments using SYNSORB and Enterotoxigenic E. coli

Binding experiments were done by incubating approximately $10^5$ CFU of enterotoxigenic E. coli in 0.5 ml of PBS containing 0.5% (w/v) mannose with SYNSORBs 16, 41, 57, 72, 75 or 88 (20 mg) and Chromosorb for 30 min. at room temperature. A control isolate EEU 351, H10407 P- which does not express CFA pili was included to demonstrate that the binding of enterotoxigenic E. coli to the surface of SYNSORB was mediated by pili. After extensive washing of the SYNSORB with PBS (about 20 ml) to remove non-adherent organisms, the SYNSORB was suspended in 1 ml of 0.5% (w/v) carboxymethyl cellulose and two dilutions of the suspension were plated on tryptic soy agar plates. After 24 h the plates were counted to determine the number of found enterotoxigenic E. coli.

The results in FIGS. 3–5 show that enterotoxigenic E. coli can effectively bind to the surface of SYNSORB. The results also indicate that several oligosaccharide structures were found to effectively bind these E. coli. The binding to SYNSORB is related to the oligosaccharide sequences found on SYNSORB since there is a significant difference between organism binding to SYNSORB and Chromosorb P alone. The results in FIGS. 3–5 represent an average of at least 4 determinations.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

TABLE 1

SYNSORBs Utilized in Heat-Labile Toxin Neutralization Studies

| SYNSORB Number | Structure Number | Common Name | Oligosaccharide Structure* |
|---|---|---|---|
| 16 | 1 | lactose | βGal(1–4)βGlc |
| 19 | 2 | — | βGal |
| 41 | 3 | — | βGal(1–3)βGalNAc |
| 57 | 4 | — | βGalNAc(1–4)βGal |
| 75 | 5 | — | βGal(1–3)βGalNAc(1–4)βGal |
| 88 | 6 | — | αNeuAc(2–3)βGal |
| 72 | 7 | — | βGal(1–3)βGal |

*All oligosaccharides are linked to Chromosorb P through a hydrophobic 8 carbon spacer arm. NeuAc is the abbreviation for sialic acid.

TABLE 2

Neutralization of Heat Labile Toxin from Enterotoxigenic E. coli Clinical Isolates.

| Isolate Number | Serotype | SYN-SORB 16* | SYN-SORB 41* | SYN-SORB 75* | SYN-SORB 88* |
|---|---|---|---|---|---|
| EEU 320 | $O_{78}H_{11}$ H10407 | 89 | 89 | 89 | 89 |
| EEU 324 | $O_{78}H_{12}$ 408-3 | 75 | 75 | 75 | 75 |
| EEU 346 | $O_6H_{16}$ | 75 | 75 | 100 | 100 |
| EEU 348 | $O_6H_{16}$ | 88 | 75 | 100 | 100 |
| EEU 351 | $O_{78}H_{11}$ H10407-P- | 88 | 75 | 50 | 75 |

*Percent Neutralization of Isolate (n = 2)
**Neutralization experiments were done using either Chinese hamster ovary (CHO) or human colonic adenocarcinoma (HT 29) tissue culture cells. Polymyxin extracts of enterotoxigenic E. coli clinical isolates were prepared and incubated with SYNSORB for 1 hour at room temperature. Percent neutralization was determined by comparing end point dilution titers from extracts that have been treated with SYNSORB with untreated samples. All experiments were done in duplicate.

What is claimed is:

1. A method to treat traveller's diarrhea mediated by E. coli heat-labile toxin (LT) in a subject, which method comprises orally administering to a subject in need of such treatment an effective amount of a composition comprising a pharmaceutically acceptable carrier in admixture with an oligosaccharide sequence covalently attached to a pharmaceutically acceptable solid, inert support through a non-peptidyl compatible linker arm, wherein said oligosaccharide sequence binds LT, and wherein said composition is capable of being eliminated from the gastrointestinal tract.

2. The method of claim 1, wherein said oligosaccharide sequence has from 1 to 3 saccharide units.

3. The method of claim 1 wherein said oligosaccharide sequence is selected from the group consisting of βGal(1–3)βGalNAc(1–4)βGal(1–3)βGalNAcβGal, αNeuAc(2–3)βGal and βGal(1–3)βGal.

4. The method of claim 1 wherein said oligosaccharide sequence covalently attached to a pharmaceutically acceptable solid, inert support through a non-peptidyl compatible linker arm is selected from the group consisting of βGal(1–3)βGalNAc, βGal(1–3)βGalNAc(1–4)βGal, αNeuAc(2–3)βGal and βGal(1–3)βGal covalently attached to Chromosorb P™.

5. The method of claim 1 wherein said linker arm is —(CH$_2$)$_8$C(O)—.

6. A pharmaceutical composition useful in treating traveller's diarrhea and related conditions initiated by *E. coli* heat-labile toxin (LT) which composition comprises:

a) an oligosaccharide sequence covalently attached to a pharmaceutically acceptable solid, inert support through a non-peptidyl compatible linker arm, wherein said oligosaccharide sequence binds LT; and b) a pharmaceutically acceptable carrier suitable for oral administration, wherein said composition is capable of being eliminated from the gastrointestinal tract.

7. The composition of claim 6 wherein said oligosaccharide sequence has from 1 to 3 saccharide units.

8. The composition of claim 6 wherein said oligosaccharide sequence is selected from the group consisting of βGal(1–3)βGalNAc(1–4)βGal(1–3)βGalNAcβGal, αNeuAc(2–3)βGal and βGal(1–3)βGal.

9. The composition of claim 6 wherein said oligosaccharide sequence covalently attached to said pharmaceutically acceptable solid, inert support through a non-peptidyl compatible linker is selected from the group consisting of β-Gal(1–3)βGalNAc, βGal(1–3)βGalNAc(1–4)βGal, αNeuAc(2–3)βGal and βGal(1–3)βGal covalently attached to Chromosorb P™.

10. The composition of claim 6 wherein said linker arm is —(CH$_2$)$_8$C(O)—.

11. A method to bind and remove LT from a sample suspected of containing said LT, which method comprises:

a) contacting said sample with an oligosaccharide sequence covalently attached to a solid, inert support through a non-peptidyl compatible linker arm, wherein said oligosaccharide sequence binds LT, under conditions wherein said LT is absorbed to said support; and b) separating the support containing the absorbed LT from the sample.

12. The method of claim 11 wherein said oligosaccharide sequence has from 1 to 3 saccharide units.

13. The method of claim 11 wherein said oligosaccharide sequence is selected from the group consisting of βGal(1–3)βGalNAc(1–4)βGal(1–3)βGalNAcβGal, αNeuAc(2–3)βGal and βGal(1–3)βGal.

14. The method of claim 11 wherein said oligosaccharide sequence covalently attached to a solid, inert support through a non-peptidyl compatible linker arm is selected from the group consisting of β-Gal(1–3)βGalNAc, βGal(1–3)βGalNAc(1–4)βGal, αNeuAc(2–3)βGal and βGal(1–3)βGal covalently attached to Chromosorb P™.

15. The method of claim 1 wherein said linker arm is —(CH$_2$)$_8$C(O)—.

* * * * *